United States Patent [19]

Tanaka et al.

[11] Patent Number: 5,789,507
[45] Date of Patent: Aug. 4, 1998

[54] METHOD FOR PREPARING WATER ABSORBENT RESIN

[75] Inventors: Keiji Tanaka, Kyoto-fu; Masashi Date; Satoshi Tamabuchi, both of Osaka-fu; Tsuyoshi Yuki; Kenjiro Tsubota, both of Kyoto, all of Japan

[73] Assignee: Sanyo Chemical Industries, Ltd., Kyoto-fu, Japan

[21] Appl. No.: 713,595

[22] Filed: Sep. 13, 1996

Related U.S. Application Data

[63] Continuation of Ser. No. 613,363, Mar. 11, 1996, abandoned.

[30] Foreign Application Priority Data

Mar. 15, 1995 [JP] Japan .................................. 7-084650

[51] Int. Cl.$^6$ .......................... C08F 2/38; G08G 63/91; C08L 3/00
[52] U.S. Cl. .................... 526/222; 526/224; 526/227; 526/238; 526/930; 523/105; 524/916; 525/54.3; 525/54.31
[58] Field of Search .................... 526/222, 234, 526/238.23, 224, 227; 523/105; 525/54.3

[56] References Cited

U.S. PATENT DOCUMENTS

| | | | |
|---|---|---|---|
| 4,076,663 | 2/1978 | Masuda et al. | 525/54.31 |
| 4,107,156 | 8/1978 | Sunamori et al. | 526/234 |
| 4,281,233 | 7/1981 | Coupek et al. | 525/54.3 |
| 4,654,038 | 3/1987 | Brandt et al. | 526/207 |
| 4,663,163 | 5/1987 | Hou et al. | 424/401 |
| 4,977,892 | 12/1990 | Ewall | 523/105 |
| 5,331,021 | 7/1994 | Ahmed et al. | 523/105 |

FOREIGN PATENT DOCUMENTS 2-300210  12/1990  Japan .

*Primary Examiner*—Tae Yoon
*Attorney, Agent, or Firm*—Merhcant, Gould, Smith, Edell, Welter & Schmidt, P.A.

[57] ABSTRACT

A method for preparing water-absorbent resins (D) by radically polymerizing a water soluble monomer (A), or a water-soluble monomer (A) and a polysaccharide (B) in the presence of a crosslinking agent (C) and water, wherein the polymerization is conducted under the existence of a thiol compound (E). Water-absorbent resins obtained in the method of the present invention provide high absorption while providing safety with very little amount of a water-soluble component.

9 Claims, No Drawings

METHOD FOR PREPARING WATER ABSORBENT RESIN

This is a continuation of application Ser. No. 08/613,363, filed Mar. 11, 1996 now abandoned.

BACKGROUND OF THE INVENTION

1. Field of the Invention

The present invention relates to a method for preparing water absorbent resins.

2. Description of the Prior Art

Theoretically, the water absorbency of water absorbent resins is, in general, in proportion to "(ion osmotic pressure+ affinity of polymer chain to water)/crosslinking density of polymer". Accordingly, water absorbent resins are produced by polymerizing water-soluble monomers to an appropriate crosslinking degree with a crosslinking agent or a grafting agent. The adjustment of crosslinking degree is controlled by the amount of a crosslinking agent or a grafting agent, the polymerization concentration (concentration of the monomer composition to be polymerized), polymerization temperature and the kind of polymerization catalysts.

However, it is difficult to prevent efficiently the self-crosslinking caused by chain transfer of polymerization propagating radicals with the above mentioned method, and thus deterioration of absorbing ability cannot be avoided. For example, if the concentration of monomer composition to be polymerized is lowered, although the absorbing ability can be restored by the reduction of self-crosslinking, problems including productivity decrease occur. Or if the crosslinking agent is reduced, although the absorbing amount can increase, the water-soluble component of the final product increases to cause problems with respect to safety such as irritation to skin when the product is used for application in contact with a human body or food.

SUMMARY OF THE INVENTION

An object of the present invention is to provide a method for preparing water absorbent resins having a high absorbing amount and capable of reducing a water-soluble component to solve the above mentioned problems.

That is, the present invention provides a method for preparing water-absorbent resins (D) which comprises radically polymerizing a water-soluble monomer (A), or a water-soluble monomer (A) and a polysaccharide (B), in the presence of a crosslinking agent (C) and water, wherein the polymerization is conducted in the presence of a thiol compound (E).

DETAILED DESCRIPTION OF THE INVENTION

Examples of the water soluble monomers (A) include at least one selected from the group consisting of monomers containing a polymerizable unsaturated group and an acid group, such as a carboxylic acid group, a sulfonic acid group and a phosphoric acid group, and water soluble salts of these monomers.

Examples of monomers containing a polymerizable unsaturated group having a carboxylic acid group include unsaturated mono- or poly- carboxylic acids such as (meth) acrylic acid (this term denotes acrylic acid and/or methacrylic acid. The same is applied hereinafter.), crotonic acid, sorbic acid, maleic acid, itaconic acid and cinnamic acid, and anhydrides of these monomers such as maleic anhydride.

Examples of monomers containing a polymerizable unsaturated group having a sulfonic acid group include aliphatic or aromatic vinyl sulfonic acids such as vinyl sulfonic acid, allyl sulfonic acid, vinyl toluene sulfonic acid and styrene sulfonic acid, (meth)acryl alkyl sulfonic acids such as sulfoethyl (meth)acrylate and sulfopropyl (meth) acrylate, and (meth)acrylamide alkyl sulfonic acids such as 2-acrylamide-2-methylpropane sulfonic acid.

Examples of monomers containing a polymerizable unsaturated group having a phosphoric acid group include phosphoric acid monoesters of hydroxy alkyl (meth)acrylate such as 2-hydroxyethyl (meth)acryloyl phosphate and phenyl-2-acryloyloxy ethylphosphate.

Monomers containing a polymerizable unsaturated group having these acid groups may be used either alone or in a combination of two or more.

Among these examples, monomers containing polymerizable unsaturated group having a carboxylic acid group or a sulfonic acid group are preferable, in particular, monomers containing polymerizable unsaturated group having a carboxylic acid group are particularly preferable.

Monomers containing a polymerizable unsaturated group having an acid group can be used in a form of their water-soluble salts. Examples of such salts include alkaline metal salts such as salts of sodium, potassium and lithium, alkaline earth metal salts such as salts of calcium and magnesium, ammonium salts and amine salts such as salts of alkylamines including methyl amine and trimethyl amine, and salts of alkanol amines including triethanol amine and diethanol amine, and a combination of two or more of these. Among these examples, sodium salt and potassium salt are preferable.

As to the neutralization degree of monomers containing a polymerizable unsaturated group having an acid group, the amount of salt in the acid group of the polymer is, in general, 50 to 90 mole %, preferably 60 to 80 mole %. A neutralization degree from 50 to 90 mole % is preferable since the viscosity of the obtained hydrogel polymer does not become too large, thus enabling the efficient production of the water absorbent resin. Further, it is also preferable with respect to safety since the pH of the obtained polymer does not become very high and therefore does not irritate human skin.

This neutralization can be conducted at any stage of the production process of water absorbent resins, for example, at the stage of monomers having a polymerizable unsaturated group or at the stage of a hydrogel as a polymerization product.

In the present invention, a polysaccharide (B) can be optionally added to water soluble monomers (A). Examples of such polysaccharides (B) include starches and celluloses. Examples of starches include raw starches such as sweet potato starch, potato starch, wheat starch, corn starch and rice starch; processed starches such as oxidized starch, dialdehyde starch, alkyl etherified starch, allyletherified starch, oxyalkylated starch and aminoethyl etherified starch.

Examples of celluloses include celluloses obtained from lumber, leaves, stalks, basts and seed fibers, and processed celluloses such as alkyl etherified cellulose, organic acid esterified cellulose, oxidized cellulose and hydroxyalkyl etherified cellulose.

When a polysaccharide (B) is used, the ratio of (B) to a water-soluble monomer having a polymerizable unsaturated group (A) is, in general, from 0.1 to 30 weight %, preferably from 3 to 20 weight %. A polysaccharide within this range is preferable, since deterioration of the water absorbing ability of the obtained water-absorbing resin can be prevented.

Examples of crosslinking agents (C) in the present invention include compounds having two polymerized double bonds (C-1) and compounds having at least one polymerized double bond and at least one functional group reactive with the water-soluble monomer (A) (C-2).

Examples of the above-mentioned crosslinking agents (C-1) include the following:

① bis(meth)acrylamide:

N,N'-alkylene bis(meth)acryl amide having an alkylene group of from 1 to 6 carbon atoms, such as N,N'-methylene bisacryl amide.

② di- or poly- ester of polyols and unsaturated mono- or polycarboxylic acid:

di- or tri- (meth)acrylate of polyols (such as ethylene glycol, trimethylol propane, glycerol, polyoxyethylene glycol and polyoxy propylene glycol) ;

unsaturated polyesters (obtained by the reaction of the above-mentioned polyols and an unsaturated acid such as maleic acid) ;

and di- or tri- (meth)acrylate (obtained by the reaction of polyepoxide and (meth)acrylic acid).

③ carbamyl ester:

carbamyl ester obtained by the reaction of hydroxyethyl (meth)acrylate and a polyisocyanate {such as tolylene diisocyanate, hexamethylene diisocyanate, 4,4'-diphenyl methane diisocyanate, and NCO group-containing prepolymers (obtained by the reaction of the above-mentioned polyisocyanates and a compound having an active hydrogen atom)}.

④ di- or poly- vinyl compound:

such as divinyl benzene, divinyl toluene, divinyl xylene, divinyl ether, divinyl ketone and trivinyl benzene.

⑤ di- or poly- (meth)allyl ether of polyols:

di- or poly- (meth)allyl ether of polyols such as alkylene glycol having 2 to 4 carbon atoms, glycerol, polyalkylene glycol having an alkylene group of 2 to 4 carbon atoms, polyalkylene polyol having an alkylene group of 2 to 4 carbon atoms and carbohydrate. For example, polyethylene glycol diallyl ether, allylated starch and allylated cellulose are included.

⑥ di- or poly- allylester of polycarboxylic acid:

such as diallyl phthalate and diallyl adipate.

⑦ ester of unsaturated mono- or poly- carboxylic acid and mono(meth)allyl ether of polyol:

such as (meth)acrylate of polyethylene glycol monoallyl ether.

⑧ allyloxy alkanes such as tetra allyloxy ethane.

Examples of the crosslinking agents (C-2) include ethylenically unsaturated compounds having a group reactive with (meth)acrylic acid and/or other copolymerizable monomers, in other words, an ethylenically unsaturated compound having a group reactive with a group such as a carboxyl group or carboxylic anhydride group, (for example, a hydroxyl group, an epoxy group and a cationic group). Concrete examples include unsaturated compounds having a nonionic group, including unsaturated compounds having a hydroxy group such as N-methylol (meth)acrylamide, unsaturated compounds having an epoxy group such as glycidyl (meth)acrylate, unsaturated compounds having a cationic group including unsaturated compounds having a quaternary ammonium salt group such as N,N,N-trimethyl-N-(meth)acryloyloxyethyl trimethyl ammonium chloride, and N,N, N-trimethyl-N-(meth)acryloyloxyethyl ammonium chloride, and unsaturated compounds having a tertiary amino group such as dimethyl amino ethyl (meth)acrylate and diethyl amino ethyl (meth)acrylate.

The above-mentioned crosslinking agents (C-1), (C-2) can be used in a combination of two or more.

In crosslinking agents (C), crosslinking agents (C-1) are preferable. In particular, bis(meth)acrylamide, di- or polyester of polyols with unsaturated monocarboxylic acids and allyloxy alkanes are preferable. Further, N,N-methylene bisacryl amide, ethylene glycol diacrylate, trimethylol propane triacrylate and tetra allyloxy ethane are more preferable.

The ratio of the crosslinking agent (C) to the total weight of the water-soluble monomer (A) and crosslinking agent (C) is, in general, from 0.0001 to 10 weight %, preferably from 0.001 to 5 weight %, more preferably from 0.01 to 2 weight %. It is preferable to have 0.0001 weight % or more of a crosslinking agent since the obtained resin can have a large gel strength at the time of water absorption without forming a sol. On the other hand, it is preferable to have 10 weight % or less of a crosslinking agent since the absorbing ability of the obtained gel does not deteriorate due to excessive gel strength.

As the method of radical polymerization in the presence of water in the present invention, a conventional method can be used. Examples of such conventional polymerization methods include aqueous solution polymerization, suspension polymerization, and reverse phase suspension polymerization using a radical polymerization catalyst. Further, as a method of initiating polymerization, a method of irradiating a radioactive ray, electron beam or ultraviolet ray can be adopted. The amount of water in polymerization is not particularly limited but in general, approximately 60 to 90 weight %, preferably 65 to 85 weight % based on the total weight of (A) to (C) and water.

Examples of radical polymerization catalysts optionally used include azo compounds such as azobisisobutyronitrile, azobiscyanovaleric acid and 2,2'-azobis(2-amidinopropane) hydrochloride, inorganic peroxides such as hydrogen peroxide, ammonium persulfate, potassium persulfate and sodium persulfate, organic peroxides such as benzoyl peroxide, di-t-butyl peroxide, cumene hydro peroxide, succinic peroxide and di(2-ethoxy ethyl)peroxydicarbonate, and redox catalysts such as those comprising a combination of a reducing agent (including a sulfite or a bisulfite salt of an alkali metal, ammonium sulfite, ammonium bisulfite, ascorbic acid), and an oxidizing agent (including persulfate of an alkali metal, ammonium persulfate, peroxides), and the combination of two or more of these.

Redox catalysts comprising a combination of hydrogen peroxide and ascorbic acid, or sodium persulfate and sodium bisulfite can be used as well.

The amount of the catalysts is similar to that used in conventional polymerization methods, in general, from 0.0001 to 5 weight %, preferably from 0.0005 to 1 weight % based on the total weight of the polymerizable water-soluble monomer (A) and the crosslinking agent (C).

Conventional conditions can be applied in terms of other polymerization conditions such as polymerization concentration, polymerization initiating temperature, polymerization time and maturing temperature.

It is preferable that water-soluble thiol compounds (E) used in the present invention are highly soluble in water and have a solubility of 1 weight % or more to a 20 weight % concentration aqueous solution of acetic acid. Water soluble thiol compounds having low volatility are preferable in terms of odor.

Water soluble thiol compounds (E) include alkylene glycol derivatives containing a thiol group (E-1) represented by the general formula (1), carboxylate derivatives containing a thiol group (E-2) represented by the general formula (2), and carboxylic acid derivatives containing a thiol group (E-3) represented by the general formula (3).

Compounds (E-1) are represented by formula (1)

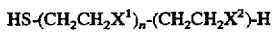

wherein : $X^1$, $X^2$ is O or S;

n is a positive integer; and m is 0 or a positive integer.

Compounds (E-2) are represented by formula (2)

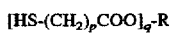

wherein : p, q is a positive integer; and

R is a residue of an aliphatic monool or an aliphatic polyol.

Compounds (E-3) are represented by formula (3)

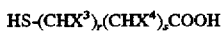

wherein : $X^3$ is H or COOH;

$X^4$ is H or SH;

r is 0 or a positive integer; and s is a positive integer.

In the above mentioned formula (1), n is, in general, 1 to 10, preferably 1 to 5; and m is, in general, 0 to 10, preferably 0 to 2. In the above mentioned formula (2), the carbon number of R is, in general, 1 to 50, preferably 2 to 10; p is, in general, 1 to 3, preferably 1 to 2; and q is, in general, 1 to 6, preferably 2 to 5. In the above mentioned formula (3), r is 0 to 2, preferably 0 or 1; and s is 1 or 2.

Concrete examples of alkylene glycol derivatives containing a thiol group (E-1) include mercaptoethanol, triethylene glycol dithiol and polyethylene glycol of molecular weight of approximately 200 to 1000 having one end or both ends modified with SH. Concrete examples of carboxylate derivatives containing a thiol group (E-2) include esters of polyethylene glycol of molecular weight of approximately 200 to 1000 and thioglycolic acid, esters of polyethylene glycol of molecular weight of approximately 200 to 1000 and thiopropionic acid, and esters of pentaerythritol and thiopropionic acid. Concrete examples of carboxylic acid derivatives containing a thiol group (E-3) include thioglycolic acid, thiopropionic acid, thiomalic acid and dithiosuccinic acid. Among these examples, (E-1) and (E-2) compounds are preferable, and (E-1) compounds are particularly preferable.

The amount of these water soluble thiol compounds (E) used in the present invention is, in general, from 0.001 to 8 weight %, preferably from 0.005 to 5 weight % based on the total weight of water soluble monomers having a polymerizable unsaturated group (A) and a crosslinking agent (C). It is preferable that the amount is 0.001 weight % or more because it achieves the desired effect of the present invention sufficiently to obtain a water absorbent resin having a high water absorbing ability with little water soluble component. Further, it is preferable that the amount is 8 weight % or less because it enables a reduction in self-crosslinking sufficiently and prevents increase of a water soluble component.

Since a thiol compound (E) works as a self-crosslinking reducer in the present invention, it is necessary that (E) is present in a polymerization system in the process of the radical polymerization. Therefore, it is preferable to add a thiol compound (E) to the polymerization system either before initializing polymerization, or at the time of polymerization. The thiol compounds (E) remain in the obtained water-absorbing polymer due to a melcapto group in a thiol compound (E) concerning the radical polymerization.

A water containing water absorbent resin (D) after polymerization can be dried and pulverized by a conventional method. Examples of drying methods include a method of loading the material on porous plates, wire gauzes, flat plates, or belts and drying by each batch or drying continuously, a method of hot-air drying in a rotary kiln or a fluidized drying oven, a method of heat drying by contacting to the surface of a hot plate or a hot roller and a method of heat drying with reduced pressure.

The surface of the water absorbent resin composition particles obtained in the present invention may be further processed by conventional surface crosslinking using a cross linking agent such as a polyglycidyl ether compound or a polyvalent metal compound.

Since water absorbent resins of the present invention obtained as heretofore mentioned reduce self-crosslinking, and achieve an optimum net structure of a polymer chain generated by polymerization of monomers and an optional crosslinking agent or graft agent, they provide high absorbing ability.

The present invention will be further illustrated with reference to Examples and Comparative Examples, however, the present invention is not limited to the embodiments described herein.

The water-solubility of a self-crosslinking reducer such as a thiol compound, and the absorbing amount and the water-soluble component amount of the water absorbing resin composition described in the Examples and the Comparative Examples are the values calculated by the following operation.

<Water-solubility>

0.1 g of a self-crosslinking reducer was gradually added to 10 g of a 20 weight % concentration aqueous solution of acetic acid at 25° C. with stirring. The appearance was visually observed and judged in terms of dissolving, deposition and cloudiness.

<Water-soluble component amount>

A figure after extracting for 3 hours was determined as the water-soluble component amount according to the method of the "Extractable Polymer Content Determination" disclosed at P.23 L.4 of the left-upper column to P.24 the sixth line from the bottom of the right-lower column of JP-A-62-54751 (Column 21, line 5 to column 23 line 50 of the corresponding U.S. Pat. No. 4,654,039).

<Absorbing amount>

1.00 g of the water absorbing resin exactly measured was placed in a 250 mesh nylon tea bag and immersed in a 0.9 weight % aqueous solution of sodium chloride for one hour. After draining for 15 minutes, the weight (a) g was measured. Also, the same procedure was conducted with the bag not having the sample therein and the weight (b) g was measured. The absorbing amount was calculated from the below-mentioned formula.

Absorbing amount (g/g)=((a)−(b))−1 +de

EXAMPLE 1

① 196g of acrylic acid, 0.05 g of methylenebisacrylamide, 675 g of deionized water, and 0.04 g of triethylene glycol dimercaptane (commerically available from Elf Atochem) were mixed and the polymerizable monomer solution was prepared. The mixture liquid was placed in a polymerizing container which allows adiabatic polymerization. By keeping the temperature at 5° C. or less and introducing nitrogen gas thereto, the dissolved oxygen amount in the solution was reduced to 1 ppm or less. Then 0.03 g of a 35% aqueous solution of hydrogen peroxide, 0.005 g of ascorbic acid, and 0.05 g of 2,2'-azobis(2-methylpropionamidine)dihydrochloride (azo catalyst, "V-50" commercially available from Wako Pure Chemical Industries, Ltd.) were added thereto. After 10 minutes a temperature rise to show the initiation of polymerization was observed. And approximately after 3 hours the solution reached equilibrium at 65° C. After 4 hour maturation, the polymerized hydrogel was obtained.

② After pulverizing 600 g of the polymerized hydrogel with a meat grinder, 165 g of an aqueous solution of NaOH of 48 weight % concentration was added thereto and further homogenously mixed by means of the meat grinder. The obtained neutralized gel was dried with hot-air at 130° C. followed by pulverization by means of a mixer for domestic use to a particle size of 20 mesh or smaller, and a water absorbent resin of the present invention was obtained. The solubility of the water-soluble thiol compound in a 20 weight % aqueous solution of acetic acid, the absorption amount and the water-soluble component amount of this water-soluble resin are described in Table 1.

EXAMPLES 2–3

Water-absorbing resins of the present invention were obtained using the same conditions as Example 1 except for the kind and the amount of each thiol compound added to the polymerizable monomer solution. The solubility of a water-soluble thiol compound in a 20 weight % aqueous solution of acetic acid, the absorption amount of this water-soluble resin and the water-soluble component amount were measured. The results are described in Table 1.

COMPARATIVE EXAMPLE 1

The result of the case when a water-soluble thiol compound (E-1) was not added in Example 1 is described in Table 1.

COMPARATIVE EXAMPLE 2

The result of the case when sodium hypophosphite was added instead of water-soluble thiol compound (E-1) is described in Table 1.

COMPARATIVE EXAMPLE 3

The result of the case when 0.04 g of a compound of ethylene glycol 2 mols adduct of bisphenol A having both ends modified with an SH group (hereinafter abbreviated BPES) was added instead of water-soluble thiol compound (E-1) is described in Table 1.

TABLE 1

| | self-crosslinking reduction agent | | absorbing amount (ml/g) | water soluble component amount (weight %) |
|---|---|---|---|---|
| | kind | solubility (weight %) | | |
| Example 1 | E-1 | transparent dissolved | 68 | 3 |
| Example 2 | E-2 | transparent dissolved | 67 | 3 |

TABLE 1-continued

| | self-crosslinking reduction agent | | absorbing amount (ml/g) | water soluble component amount (weight %) |
|---|---|---|---|---|
| | kind | solubility (weight %) | | |
| Example 3 | E-3 | transparent dissolved | 66 | 4 |
| Comparative Example 1 | not added | — | 54 | 5 |
| Comparative Example 2 | sodium hypophosphite | transparent dissolved | 59 | 11 |
| Comparative Example 3 | BPES | cloudy deposited | 53 | 6 |

E-1: triethylene glycol dimelcaptane
E-2: diester of polyethylene glycol with thiopropionic acid
E-3: thioglycolic acid
BPES: ethylene glycol 2 mols adduct of bisphenol A having both ends modified with thiol Water absorbent resins obtained in the method of the present invention have high absorbing amount with very little water soluble component. Since water absorbent resins of the present invention have the above-mentioned advantages, they are useful in various industrial applications such as; an application in contact with a human body such as water-absorbing pads and hygienic materials including disposable diapers for infants or adults, sanitary napkins, hygienic cottons, bandages, incontinence pads and paper towels; an application with possiblity of contacting foods such as freshness retaining materials for vegetables and fruits or drip absorbing materials for meat or marine products; an application for water retaining materials for plants or soils; and an application for anti-dewing materials for interior materials of construction.

We claim:

1. A method for preparing water absorbent resins (D) comprising radically polymerizing a water-soluble monomer (A), or a water-soluble monomer (A) and a polysaccharide (B), and a crosslinking agent (C) in the presence of water, a water-soluble thiol compound (E) and a radical polymerization catalyst (F), wherein said thiol compound (E) has a solubility of 1 weight % or more to a 20 weight % aqueous solution of acetic acid, and said radical polymerization catalyst (F) is at least one selected from the group consisting of azo compounds, inorganic peroxides, organic peroxides, and redox catalysts comprising a combination of a reducing agent and an oxidizing agent.

2. The method for preparing water-absorbent resin according to claim 1, wherein the crosslinking agent (C) is at least one selected from the group consisting of a compound (C-1) having two polymerizable double bonds and a compound (C-2) having at least one polymerizable double bond and at least one functional group reactive with the water-soluble monomer (A).

3. The method for preparing water-absorbent resins according to claim 1, wherein the thiol compound (E) is at least one compound selected from the group consisting of the following formulae (1) to (3):

$$HS\text{-}(CH_2CH_2X^1)_n\text{-}(CH_2CH_2X^2)_m\text{-}H \qquad (1)$$

wherein : $X^1$, $X^2$ is O or S;
n is a positive integer; and
m is 0 or a positive integer;

$$[HS\text{-}(CH_2)_p COO]_q\text{-}R \quad (2)$$

wherein : p, q is a positive integer;

R is a residue of an aliphatic monool or an aliphatic polyol; and $$HS\text{-}(CHX^3)_r(CHX^4)_s COOH \quad (3)$$

wherein : $X^3$ is H or COOH;

$X^4$ is H or SH;

r is 0 or a positive integer;

s is a positive integer.

4. The method for preparing water-absorbent resins according to claim 1, wherein the water-soluble monomer (A) is at least one selected from the group consisting of ① monomers containing a polymerizable unsaturated group and an acid group selected from a carboxylic group, a sulphonic group or a phosphoric group, and ② water-soluble salts of these monomers.

5. The method for preparing water-absorbent resins according to claim 1, wherein the water-soluble monomer (A) is a monomer comprising at least one selected from the group consisting of acrylic acid, methacrylic acid and salts of these monomers.

6. The method for preparing water-absorbent resins according to claim 1, wherein the amount of the polysaccharide (B) is 30 weight % or less based on the water-soluble monomer (A).

7. The method for preparing water-absorbent resins according to claim 1, wherein the amount of the crosslinking agent (C) is 0.0001 to 10 weight % based on the total weight of the water-soluble monomer (A) and the crosslinking agent (C).

8. The method for preparing water-absorbent resins according to claim 1, wherein the amount of the thiol compound (E) is 0.01 to 8 weight % based on the total weight of the water-soluble monomer (A) and the crosslinking agent (C).

9. A water-absorbent resin prepared by the method of claim 1.

* * * * *